(12) United States Patent
Palanichamy et al.

(10) Patent No.: US 10,098,086 B2
(45) Date of Patent: Oct. 9, 2018

(54) GUIDING A USER IN A HEALTH HAZARDOUS ENVIRONMENT

(71) Applicant: HCL Technologies Limited, Uttar Pradesh (IN)

(72) Inventors: Banumathi Palanichamy, Chennai (IN); Sankareswari Amudhasidhanandham, Chennai (IN); AnbuSelvan Vetriselvan, Chennai (IN); Sivasakthivel Sadasivam, Chennai (IN)

(73) Assignee: HCL Technologies Limited, Noida, Uttar Pradesh ( * ) Notice: Subject to any disclaimer, the term of this patent is extended or adjusted under 35 U.S.C. 154(b) by 8 days.

(21) Appl. No.: 15/443,406

(22) Filed: Feb. 27, 2017

(65) Prior Publication Data

US 2017/0273049 A1    Sep. 21, 2017

(30) Foreign Application Priority Data

Mar. 16, 2016    (IN) .............................. 201611009173

(51) Int. Cl.
*H04W 64/00*    (2009.01)
*H04W 4/00*    (2018.01)
*H04W 4/04*    (2009.01)

(52) U.S. Cl.
CPC ........... *H04W 64/006* (2013.01); *H04W 4/04* (2013.01)

(58) Field of Classification Search
CPC .............................. H04W 64/006; H04W 4/04
USPC .................................. 455/441; 701/516, 434
See application file for complete search history.

(56) References Cited

U.S. PATENT DOCUMENTS

| 7,378,954 | B2 | 5/2008 | Wendt | |
|---|---|---|---|---|
| 9,105,171 | B2 | 8/2015 | Flood et al. | |
| 2002/0072881 | A1* | 6/2002 | Saitta | A62B 3/00 703/1 |
| 2007/0246642 | A1 | 10/2007 | Millett et al. | |
| 2009/0027216 | A1 | 1/2009 | Huang et al. | |
| 2011/0190909 | A1* | 8/2011 | Salsbury | G05B 13/02 700/42 |
| 2013/0090842 | A1* | 4/2013 | Stabile | G01C 23/00 701/123 |
| 2015/0031970 | A1 | 1/2015 | Lain | |

(Continued)

OTHER PUBLICATIONS

Airmet, "Oxygen Depletion Detection System", Jun. 24, 2009, 1 page.

*Primary Examiner* — Inder Mehra
(74) *Attorney, Agent, or Firm* — HM Law Group LLP; Vani Moodley, Esq.

(57) ABSTRACT

The present disclosure relates to system(s) and method(s) for guiding a user in changing oxygen level environment is illustrated. The system is configured to capturing a set of oxygen levels corresponding to a set of zones in a geographical area. Further, the system is configured for receiving an oxygen threshold level and a current location, corresponding to a user in the geographical area, from a user device of a user. Further, the system may identify a current oxygen level from the set of oxygen levels, wherein the current oxygen level corresponds to a zone associated with the current location of the user. Further, the system is configured to display an oxygen level map, corresponding to the geographical area, on the user device for guiding the user to reach a target zone, in the geographical area.

9 Claims, 4 Drawing Sheets

(56) References Cited

U.S. PATENT DOCUMENTS

| | | | |
|---|---|---|---|
| 2015/0223705 A1* | 8/2015 | Sadhu | G01S 19/17 600/301 |
| 2016/0127172 A1* | 5/2016 | Shaw | H04L 41/08 709/223 |
| 2017/0124276 A1* | 5/2017 | Tee | G06F 19/3418 |
| 2017/0188864 A1* | 7/2017 | Drury | A61B 5/0408 |

* cited by examiner

GUIDING A USER IN A HEALTH HAZARDOUS ENVIRONMENT

CROSS-REFERENCE TO RELATED APPLICATIONS AND PRIORITY

The present application claims priority from Indian Patent Application No. 201611009173, filed on Mar. 16, 2016, the entirety of which is hereby incorporated by reference.

TECHNICAL FIELD

The present disclosure in general relates to the field navigation. More particularly, the present invention relates to a system and method for providing navigation assistance to a user in a health hazardous environment.

BACKGROUND

For human life, oxygen is the most important element/gas. Most of the body metabolic energy is created by oxygen. Human body is adapted to extract oxygen from air by way of breathing. After breathing air, the lungs extract oxygen which is supplied to all parts of the body. Each and every cell in the body requires oxygen to function, repair, and restore by them self.

Nowadays, due to increase on air pollution, the air is polluted with harmful gases and dust. People may not know by themselves that a sufficient level of oxygen in the environment is present or not. Moreover, in closed areas like shopping malls and underground tunnels, there is a high risk of low oxygen level and may contain a high level of toxic gases in air. Due to lack of oxygen from environment, the body suffers with various health issues like suffocation, head ache, fatigue. At times it may leads to life threatening situation. The low existence of oxygen level cannot be detected by humans just by breathing the air. Many places like Malls, Theatres, temples, high altitude mountains exist, where people gather in bulk, resulting into marginal reduction in the oxygen level in a short span of time, without the knowledge of the people. For example, oxygen level may vary inside a closed room where more than four members are sleeping in the closed room, places like airport, railway station, etc.

There are systems and devices available in the art which teach towards detecting of harmful gases and low oxygen level. However, these systems can only alert the user of the health hazardous situation.

SUMMARY

This summary is provided to introduce aspects related to systems and methods for guiding a user in changing oxygen level environment and the aspects are further described below in the detailed description. This summary is not intended to identify essential features of the claimed subject matter nor is it intended for use in determining or limiting the scope of the claimed subject matter.

In one embodiment, a system for guiding a user in changing oxygen level environment is illustrated. The system comprises a processor coupled to a memory, wherein the processor is configured to execute programmed instructions stored in the memory. The processor may execute a programmed instruction for capturing a set of oxygen levels corresponding to a set of zones in a geographical area. The set of oxygen levels may be captured through a set of sensors in the geographical area. In one embodiment, each sensor from the set of oxygen sensors may be mounted over of user devices in the geographical area. Further, the processor may execute a programmed instruction for receiving an oxygen threshold level and a current location, corresponding to a user in the geographical area, from a user device of a user. Further, the processor may execute a programmed instruction for identifying a current oxygen level from the set of oxygen levels, wherein the current oxygen level corresponds to a zone associated with the current location of the user. Further, the processor may execute a programmed instruction for displaying an oxygen level map, corresponding to the geographical area, on the user device for guiding the user to reach a target zone, in the geographical area. In one embodiment, the oxygen level of the target zone may be equal to or above the oxygen threshold level.

In one embodiment, a method for guiding a user in changing oxygen level environment is illustrated. The method may comprise capturing a set of oxygen levels corresponding to a set of zones in a geographical area. The set of oxygen levels may be captured through a set of sensors in the geographical area. In one embodiment, each sensor from the set of oxygen sensors may be mounted over of user devices in the geographical area. Further, the method may comprise receiving an oxygen threshold level and a current location, corresponding to a user in the geographical area, from a user device of a user. Further, the method may comprise identifying a current oxygen level from the set of oxygen levels, wherein the current oxygen level corresponds to a zone associated with the current location of the user. Further, the method may comprise displaying an oxygen level map, corresponding to the geographical area, on the user device for guiding the user to reach a target zone, in the geographical area. In one embodiment, the oxygen level of the target zone may be equal to or above the oxygen threshold level.

In one embodiment, a non-transitory computer readable medium embodying a program executable in a computing device for guiding a user in changing oxygen level environment is disclosed. The program comprises a program code for capturing a set of oxygen levels corresponding to a set of zones in a geographical area. The set of oxygen levels may be captured through a set of sensors in the geographical area. In one embodiment, each sensor from the set of oxygen sensors may be mounted over of user devices in the geographical area. Further, the program comprises a program code for receiving an oxygen threshold level and a current location, corresponding to a user in the geographical area, from a user device of a user. Further, the program comprises a program code for identifying a current oxygen level from the set of oxygen levels, wherein the current oxygen level corresponds to a zone associated with the current location of the user. Further, the program comprises a program code for displaying an oxygen level map, corresponding to the geographical area, on the user device for guiding the user to reach a target zone, in the geographical area. In one embodiment, the oxygen level of the target zone may be equal to or above the oxygen threshold level.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Figure 1:
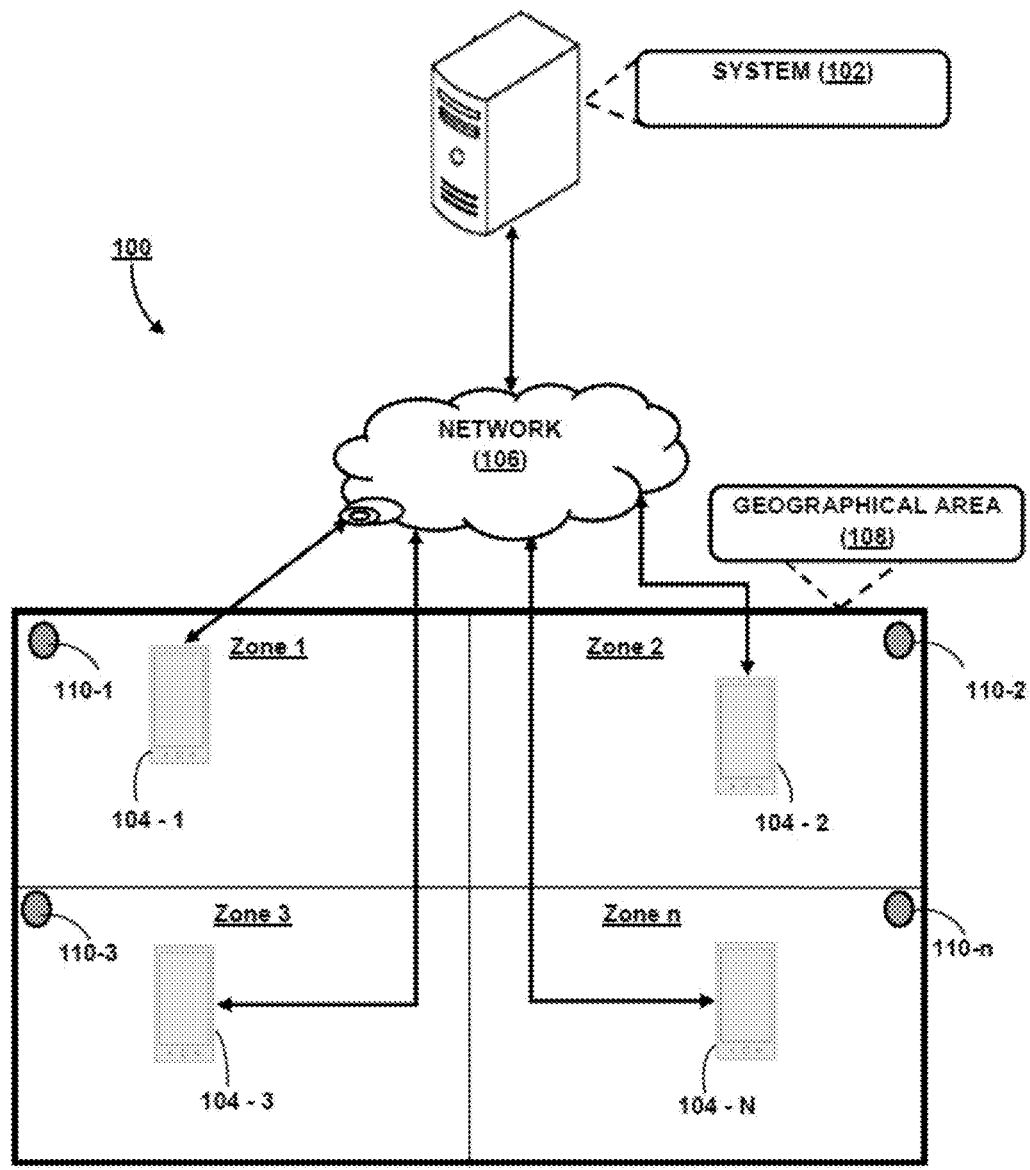
FIG. 1 illustrates a network implementation of a system for guiding a user in a changing oxygen level environment, in accordance with an embodiment of the present subject matter.

The present subject matter relates to a system for guiding a user in changing oxygen level environment. Initially, the system is configured to capture a set of oxygen levels corresponding to a set of zones in a geographical area. The set of oxygen levels may be captured through a set of sensors in the geographical area. In one embodiment, each sensor from the set of oxygen sensors may be mounted over of user devices in the geographical area. Further, the system is configured to receive an oxygen threshold level and a current location, corresponding to a user in the geographical area, from a user device of the user. Further, the system is configured to identify a current oxygen level from the set of oxygen levels, wherein the current oxygen level corresponds to a zone associated with the current location of the user. Further, the system is configured to display an oxygen level map, corresponding to the geographical area, on the user device for guiding the user to reach a target zone, in the geographical area. In one embodiment, the oxygen level of the target zone may be equal to or above the oxygen threshold level.

In one embodiment, the system is configured to direct the user to reach the target location/zone which have the required oxygen level and also provide actionable feedback/alarm message if the oxygen level in the current location/zone is decreased beyond the threshold level specified by the user. In one embodiment, the oxygen threshold level may be configured based on the user's health condition. In yet another embodiment, the system may be used to monitor other health parameters such as air pollution level, humidity level and UV level in the environment and provide navigation assistance in a closed or open geographical location.

In one embodiment, the system is configured to communicate with a set of sensing devices installed in a geographical location. Each sensing device is associated with a zone in the geographical area. Further, the sensing device is enabled with a processor, a memory and an oxygen sensor. The oxygen sensor is configured to continuously monitor the oxygen level in the zone. Further, the sensing device is configured to transmit the oxygen level to the system. Further, the system is configured to receive oxygen level information from each sensing device in the geographical area.

In one embodiment, the user device is enabled with a processor, a GPS sensor, an alarm generator and I/O interface. The user of the user device may configure their risk profile based on an oxygen threshold level, over the user device. The oxygen threshold level is indicative of a minimum oxygen level required by the user for survival. Further, the oxygen sensor in the sensing device is configured to detect the real-time oxygen level in the zone corresponding to the user and update the oxygen level to the system. Further, the system is configured to communicate with the user device and receive the oxygen threshold level. Furthermore, the system is configured to compare the threshold oxygen level of the user with the current oxygen level and generate alerts to the user if the oxygen level is below the threshold oxygen level.

Further, the system is configured to generate an oxygen level map based on oxygen levels captured from each zone in the geographical area. The system may further display the oxygen level map, corresponding to the geographical area, to the user by means of the user device. The oxygen level map is configured to display the current location of the user and the oxygen level of the different zones in the geographical area. Further, the oxygen level map is configured to assist the user to reach a target zone, in the geographical area. In one embodiment, the oxygen level of the target zone may be equal to or above the oxygen threshold level.

In one embodiment, in absence of the sensing device, the system is configured to communicate with a user device of the user. In one embodiment, the user device is enabled with a processor, an oxygen sensor/environmental sensors, and a Global Positioning System (GPS) Sensor, wherein the user device is configured to communicate with the system through a wireless communication network and transmit the oxygen level of the zone in which the user device is present. In a similar manner, oxygen level of each zone may be captured in real-time by the user devices in the geographical area and received by the system. Further, the system is configured to compare the threshold oxygen level of the user with the current oxygen level and generate alerts to the user if the oxygen level is below the threshold oxygen level. Further, the system is also configured to guide the user to reach a target zone based on the oxygen level map generated, by the system, based on the oxygen levels captured from each zone in the geographical area.

While aspects of described system and method for guiding a user in changing oxygen level environment may be implemented in any number of different computing systems, environments, and/or configurations, the embodiments are described in the context of the following exemplary system.

Referring now to FIG. 1, a network implementation 100 of a system 102 for guiding a user in changing oxygen level environment is disclosed. Although the present subject matter is explained considering that the system 102 is implemented on a server, it may be understood that the system 102 may also be implemented in a variety of computing systems, such as a laptop computer, a desktop computer, a notebook, a workstation, a mainframe computer, a server, a network server, and the like. In one implementation, the system 102 may be implemented in a cloud-based environment. It will be understood that the system 102 may be accessed by multiple users through one or more user devices 104-1, 104-2 . . . 104-N, collectively referred to as user devices 104 hereinafter, or applications residing on the user devices 104. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

In one embodiment, the system 102 is configured to communicate with a set of sensing devices 110 installed in a geographical location through the network 106. Each sensing device 110 is associated with a zone in the geographical area 108. Further, the sensing device is enabled with a processor, a memory and an oxygen sensor. The oxygen sensor is configured to continuously monitor the oxygen level in the zone corresponding to the sensing device 110. Further, the sensing device 110 is configured to transmit the oxygen level in the zone to the system 102. Further, the system 102 is configured to receive oxygen level information from each sensing device 110 in the geographical area 108.

In one embodiment, the user device 104 is enabled with a processor, a GPS sensor, an alarm generator and I/O interface. The user of the user device may configure their risk profile based on an oxygen threshold level, over the user device 104. The oxygen threshold level is indicative of a minimum oxygen level required by the user for survival. Further, the oxygen sensor in the sensing device 110 is configured to detect the real-time oxygen level in the zone corresponding to the user and update the oxygen level to the system 102. Further, the system 102 is configured to communicate with the user device and receive the oxygen threshold level. Furthermore, the system 102 is configured to compare the threshold oxygen level of the user with the current oxygen level and generate alerts to the user if the oxygen level is below the threshold oxygen level.

Further, the system 102 is configured to generate an oxygen level map based on oxygen levels captured from each zone in the geographical area 108. The system 102 may further display the oxygen level map, corresponding to the geographical area 108, to the user by means of the user device 104. The oxygen level map is configured to display the current location of the user and the oxygen level of the different zones in the geographical area 108. Further, the oxygen level map is configured to assist the user to reach a target zone, in the geographical area 108. In one embodiment, the oxygen level of the target zone may be equal to or above the oxygen threshold level.

Figure 2:
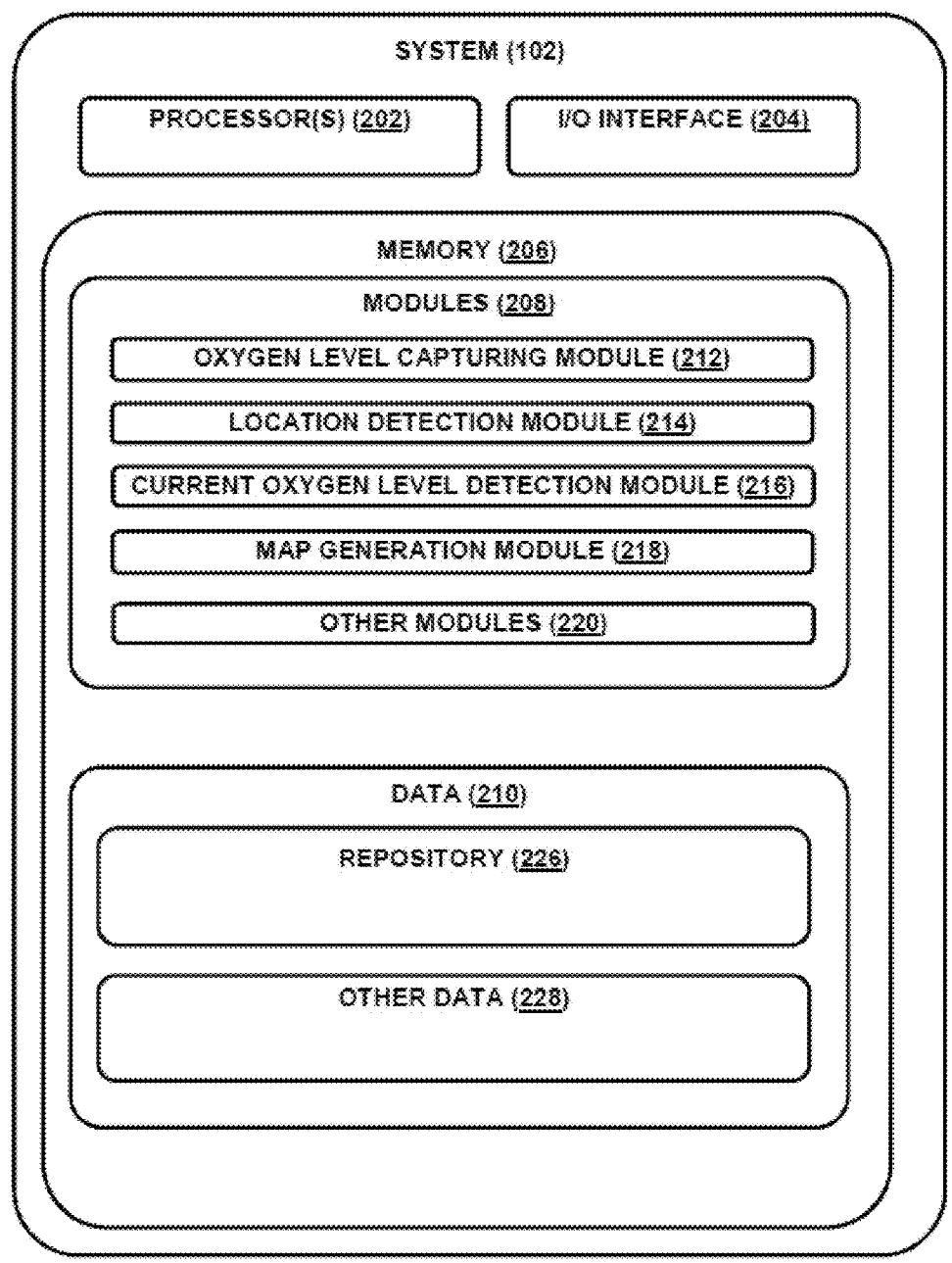
FIG. 2 illustrates the system for guiding a user in the changing oxygen level environment, in accordance with an embodiment of the present subject matter.

Referring now to FIG. 2, the system 102 is illustrated in accordance with an embodiment of the present subject matter. In one embodiment, the system 102 may include at least one processor 202, an input/output (I/O) interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with a user directly or through the client devices 104. Further, the I/O interface 204 may enable the system 102 to communicate with other computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules 208 and data 210.

The modules 208 include routines, programs, objects, components, data structures, etc., which perform particular tasks, functions or implement particular abstract data types. In one implementation, the modules 208 may include an oxygen level capturing module 212, a location detection module 214, a current oxygen level detection module 216, a map generation module 218, and other modules 220. The other modules 220 may include programs or coded instructions that supplement applications and functions of the system 102.

The data 210, amongst other things, serves as a repository for storing data processed, received, and generated by one or more of the modules 208. The data 210 may also include a repository 226, and other data 228. In one embodiment, the repository 226 may be configured to store oxygen level captured from different zones in the geographical area 108. In one embodiment, the other data 228 may include data generated as a result of the execution of one or more modules in the other module 220.

In one implementation, the process of guiding a user in changing oxygen level environment is initiated by the oxygen level capturing module 212. The oxygen level capturing module 212 is configured to capture oxygen levels corresponding to a set of zones in a geographical area. In one embodiment, the set of sensing devices 110 are used to capture the oxygen level at each zone in the geographical area 108. Each sensing device from the set of sensing devices 110 is physically located at a zone in the geographical area 108. The sensing device is enabled with an oxygen sensor, wherein the oxygen sensor is configured to continuously or periodically monitor the oxygen level in the zone and transmit this information to the system 102 through the sensing device. In a similar manner, oxygen levels associated with each zone are received from the set of sensing devices 110. In another embodiment, the oxygen level information may be gathered using a set of user devices 104 enabled with oxygen sensor in the geographical area 108. Once the oxygen level information is gathered, in the next step, the current oxygen level of each zone is maintained in the repository 228.

Further, the location detection module 214 is configured to receive an oxygen threshold level and a current location, corresponding to a user in the geographical area 108, from a user device of a set of user devices 104. The oxygen threshold level is indicative of the minimum oxygen level required by the user for survival. The current location of the user may be captured using a GPS sensor at the user device. Based on the current location, the location detection module 214 is configured to determine a current zone of the user. For example, if the current location if the user lies within the predefined boundaries of a particular zone, then the location detection module 214 identified the zone as the current zone of the user.

Further, the current oxygen level detection module 216 is configured to identify a current oxygen level from the set of oxygen levels. The current oxygen level corresponds to the current zone associated with the current location of the user. The current oxygen level is determined from the repository 228 of the system 102.

Further, the map generation module 218 is configured to display an oxygen level map, corresponding to the geographical area 108, on the user device 104 for guiding the user to reach a target zone, in the geographical area 108. In one embodiment, the oxygen level of the target zone may be equal to or above the oxygen threshold level of the user. The map generation module 218 is configured to display a map of the geographically area 108, wherein each zone in the geographical area 108 is displayed with their respective oxygen levels. Further, the map also displays the rout required to be taken by the user to reach the target zone. The method for guiding a user in changing oxygen level environment is further illustrated with respect to the block diagram of FIG. 3.

Figure 3:
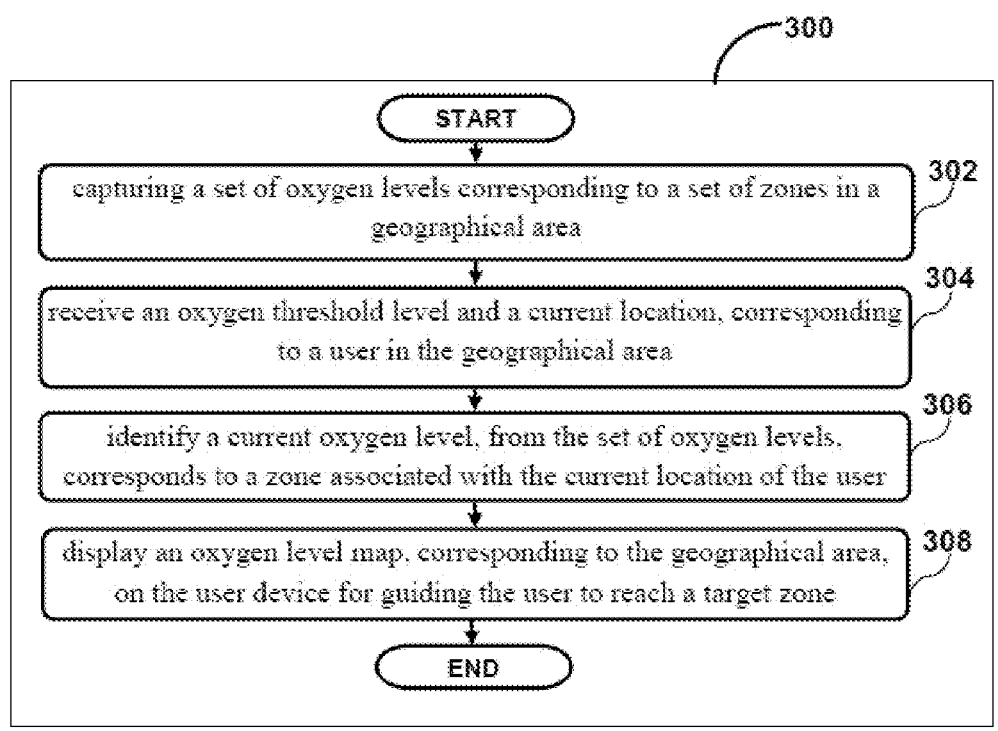
FIG. 3 illustrates a flow diagram for guiding a user in the changing oxygen level environment using the system, in accordance with an embodiment of the present subject matter.

Referring now to FIG. 3, a method 300 for guiding a user in changing oxygen level environment is disclosed, in accordance with an embodiment of the present subject matter. The method 300 may be described in the general context of computer executable instructions. Generally, computer executable instructions can include routines, programs, objects, components, data structures, procedures, modules, functions, and the like, that perform particular functions or implement particular abstract data types. The method 300 may also be practiced in a distributed computing environment where functions are performed by remote processing devices that are linked through a communications network. In a distributed computing environment, computer executable instructions may be located in both local and remote computer storage media, including memory storage devices.

The order in which the method 300 is described is not intended to be construed as a limitation, and any number of the described method blocks can be combined in any order to implement the method 300 or alternate methods. Additionally, individual blocks may be deleted from the method 300 without departing from the spirit and scope of the subject matter described herein. Furthermore, the method 300 can be implemented in any suitable hardware, software, firmware, or combination thereof. However, for ease of explanation, in the embodiments described below, the method 300 may be considered to be implemented in the above described system 102.

At block 302, the oxygen level capturing module 212 is configured to capture oxygen levels corresponding to a set of zones in a geographical area. In one embodiment, the set of sensing devices 110 are used to capture the oxygen level at each zone in the geographical area 108. Each sensing device from the set of sensing devices 110 is physically located at a zone in the geographical area 108. The sensing device is enabled with an oxygen sensor, wherein the oxygen sensor is configured to continuously or periodically monitor the oxygen level in the zone and transmit this information to the system 102 through the sensing device. In a similar manner, oxygen levels associated with each zone are received from the set of sensing devices 110. In another embodiment, the oxygen level information may be gathered using a set of user devices 104 enabled with oxygen sensor in the geographical area 108. Once the oxygen level information is gathered, in the next step, the current oxygen level of each zone is maintained in the repository 228.

At block 304, the location detection module 214 is configured to receive an oxygen threshold level and a current location, corresponding to a user in the geographical area 108, from a user device of a set of user devices 104. The oxygen threshold level is indicative of the minimum oxygen level required by the user for survival. The current location of the user may be captured using a GPS sensor at the user device. Based on the current location, the location detection module 214 is configured to determine a current zone of the user. For example, if the current location if the user lies within the predefined boundaries of a particular zone, then the location detection module 214 identified the zone as the current zone of the user.

At block 306, the current oxygen level detection module 216 is configured to identify a current oxygen level from the set of oxygen levels. The current oxygen level corresponds to the current zone associated with the current location of the user. The current oxygen level is determined from the repository 228 of the system 102.

At block 308, the map generation module 218 is configured to display an oxygen level map, corresponding to the geographical area 108, on the user device 104 for guiding the user to reach a target zone, in the geographical area 108. In one embodiment, the oxygen level of the target zone may be equal to or above the oxygen threshold level of the user. The map generation module 218 is configured to display a map of the geographically area 108, wherein each zone in the geographical area 108 is displayed with their respective oxygen levels. Further, the map also displays the rout required to be taken by the user to reach the target zone.

Figure 4:
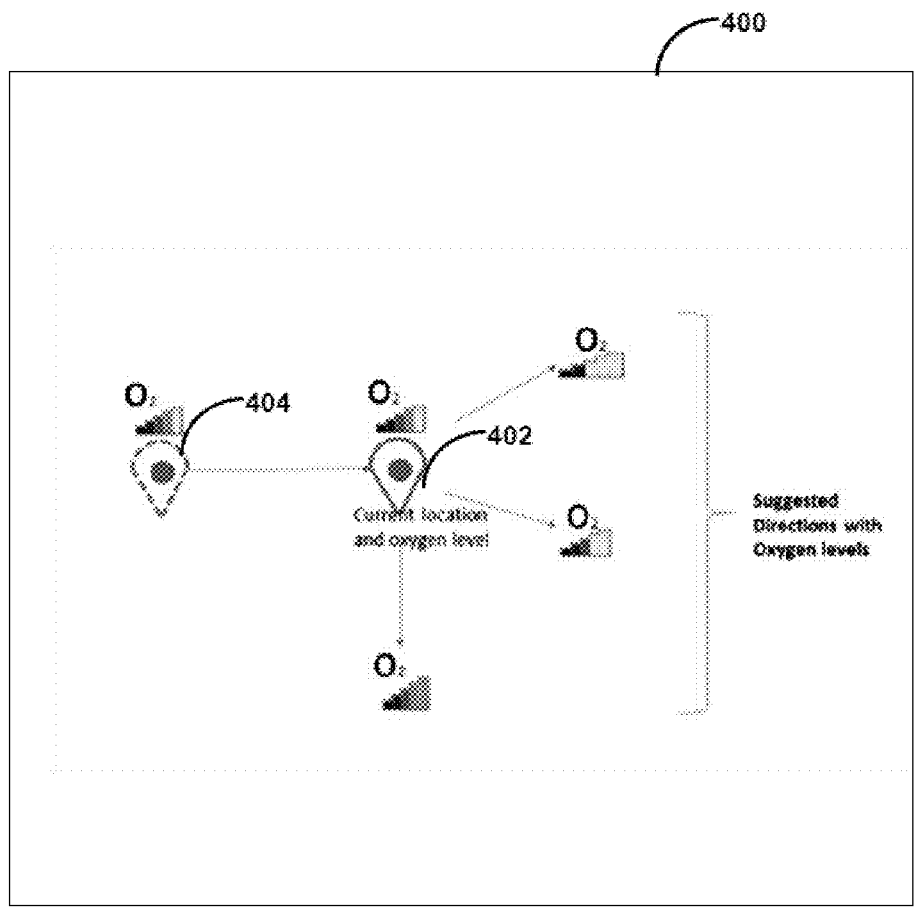
FIG. 4 illustrates a graphical user interface for guiding a user in the changing oxygen level environment using the system, in accordance with an embodiment of the present subject matter.

Referring now to FIG. 4, a graphical user interface for guiding a user in the changing oxygen level environment using the system 102 is illustrated in accordance with an embodiment of the present subject matter. The graphical user interface displays an oxygen level map 400, corresponding to the geographical area 108, on the graphical user interface of the user device 104 for guiding the user to reach a target zone, in the geographical area 108.

Although implementations for methods and systems for guiding a user in the changing oxygen level environment has been described, it is to be understood that the appended claims are not necessarily limited to the specific features or methods described. Rather, the specific features and methods are disclosed as examples of implementations for guiding a user in the changing oxygen level environment.

We claim:

1. A system for guiding a user in changing oxygen level environment, the system comprising:
   a memory;
   a processor coupled to the memory, wherein the processor is configured to execute program instructions stored in the memory to:
   capture a set of oxygen levels corresponding to a set of zones in a geographical area, wherein the set of oxygen levels is captured through a set of sensors in the geographical area, wherein the set of sensors in the geographical area are installed over a set of user devices in the geographical area;
   receive an oxygen threshold level and a current location, corresponding to a user in the geographical area, from the user device, wherein the oxygen threshold level is configured based on the health condition of the user;

identify a current oxygen level from the set of oxygen levels, wherein the current oxygen level corresponds to a zone associated with the current location of the user;

transmit one or more alerts to the user device based on the comparison of the oxygen threshold level with the current oxygen level, and display an oxygen level map, corresponding to the geographical area, when the current oxygen level is below the oxygen threshold level, wherein the oxygen level map is displayed on the user device for guiding the user to reach a target zone, in the geographical area, having the oxygen level above the oxygen threshold level.

2. The system of claim 1, wherein the current location of the user is detected, at the user device, by a GPS sensor in the user device.

3. The system of claim 1, wherein the oxygen level map is generated in real-time.

4. The system of claim 1, wherein the target zone is determined based on the comparison of oxygen threshold level with the set of oxygen levels and the current location of the user.

5. A method for guiding a user in changing oxygen level environment, the method comprising steps of:

capturing, by a processor, a set of oxygen levels corresponding to a set of zones in a geographical area, wherein the set of oxygen levels is captured through a set of sensors in the geographical area, wherein the set of sensors in the geographical area are installed over a set of user devices in the geographical area;

receiving, by the processor, an oxygen threshold level and a current location, corresponding to a user in the geographical area, from the user device, wherein the oxygen threshold level is configured based on the health condition of the user;

identifying, by the processor, a current oxygen level from the set of oxygen levels, wherein the current oxygen level corresponds to a zone associated with the current location of the user;

transmitting one or more alerts to the user device based on the comparison of the oxygen threshold level with the current oxygen level, and displaying, by the processor, an oxygen level map, corresponding to the geographical area, when the current oxygen level is below the oxygen threshold level, wherein the oxygen level map is displayed on the user device for guiding the user to reach a target zone, in the geographical area, having the oxygen level above the oxygen threshold level.

6. The method of claim 5, wherein the current location of the user is detected, at the user device, by a GPS sensor in the user device.

7. The method of claim 5, wherein the oxygen level map is generated in real- time.

8. The method of claim 5, wherein the target zone is determined based on the comparison of oxygen threshold level with the set of oxygen levels and the current location of the user.

9. A non-transitory computer readable medium embodying a program executable in a computing device for guiding a user in changing oxygen level environment, the computer program product comprising:

a program code for capturing a set of oxygen levels corresponding to a set of zones in a geographical area, wherein the set of oxygen levels is captured through a set of sensors in the geographical area, wherein the set of sensors in the geographical area are installed over a set of user devices in the geographical area;

a program code for receiving an oxygen threshold level and a current location, corresponding to a user in the geographical area, from the user device, wherein the oxygen threshold level is configured based on the health condition of the user;

a program code for identifying a current oxygen level from the set of oxygen levels, wherein the current oxygen level corresponds to a zone associated with the current location of the user; a program code for transmitting one or more alerts to the user device based on the comparison of the oxygen threshold level with the current oxygen level, and a program code for displaying an oxygen level map, corresponding to the geographical area, when the current oxygen level is below the oxygen threshold level, wherein the oxygen level map is displayed on the user device for guiding the user to reach a target zone, in the geographical area, having the oxygen level above the oxygen threshold level.

* * * * *